(12) United States Patent
Hugg et al.

(10) Patent No.: US 7,339,174 B1
(45) Date of Patent: Mar. 4, 2008

(54) COMBINED SLIT/PINHOLE COLLIMATOR METHOD AND SYSTEM

(75) Inventors: James William Hugg, Glenville, NY (US); Jorge Uribe, Niskayuna, NY (US); Floribertus P. M. Heukensfeldt Jansen, Ballston Lake, NY (US)

(73) Assignee: General Electric Company, Niskayuna, NY (US)

( * ) Notice: Subject to any disclaimer, the term of this patent is extended or adjusted under 35 U.S.C. 154(b) by 0 days.

(21) Appl. No.: 11/704,593

(22) Filed: Feb. 9, 2007

(51) Int. Cl.
*G02K 1/02* (2006.01)
(52) U.S. Cl. .............. 250/363.1; 250/362; 250/363.04
(58) Field of Classification Search .......... 250/363.01, 250/363.02, 363.03, 363.04, 363.05, 363.06, 250/363.07, 363.08, 363.09, 363.1
See application file for complete search history.

(56) References Cited

U.S. PATENT DOCUMENTS

| | | | |
|---|---|---|---|
| 4,289,965 A | 9/1981 | Koga | |
| 4,389,569 A | 6/1983 | Hattori | |
| 5,021,667 A * | 6/1991 | Genna et al. | 250/363.1 |
| 5,032,728 A | 7/1991 | Chang | |
| 6,504,157 B2 | 1/2003 | Juhi | |
| 6,525,320 B1 | 2/2003 | Juni | |
| 6,525,321 B2 | 2/2003 | Juni | |
| D474,277 S | 5/2003 | Juni | |
| D492,998 S | 7/2004 | Juni | |
| 7,012,257 B2 | 3/2006 | Juni | |
| 7,015,476 B2 | 3/2006 | Juni | |
| 7,071,473 B2 | 7/2006 | Juni | |
| 7,105,825 B2 | 9/2006 | Juni | |
| 7,138,638 B2 | 11/2006 | Juni | |
| 2004/0239941 A1 | 12/2004 | Schramm | |
| 2006/0050845 A1 | 3/2006 | Juni | |

(Continued)

FOREIGN PATENT DOCUMENTS

WO  WO 00/062093  10/2000

(Continued)

OTHER PUBLICATIONS

De Kuhl and RQ Edwards, Cylindrical and Section Radioisotope Scanning of the Liver and Brain, Radiology, 1964, vol. 83, pp. 926-935.

(Continued)

*Primary Examiner*—Kiesha L. Rose
*Assistant Examiner*—Kiho Kim
(74) *Attorney, Agent, or Firm*—Fletcher Yoder

(57) ABSTRACT

Collimator assemblies that include an inner combined collimator and an outer collimator are provided. The inner combined collimator includes a first portion having one or more slit apertures therein, and a second portion having one or more pinhole apertures therein. The outer collimator includes one or more septa spaced on a side of the first portion of the inner combined collimator. The slit apertures of the inner combined collimator and the septa of the outer collimator are arranged to define a plurality of apertures through the collimator assembly. Imaging systems that include the collimator assemblies and a detector assembly are also provided. The detector assembly may be configured to detect gamma rays emanating from a field of view that pass through apertures defined by the collimator assembly and to generate one or more signals in response to the detected gamma rays. Methods of imaging a field view using the collimating assembly are also provided.

28 Claims, 9 Drawing Sheets

U.S. PATENT DOCUMENTS

2006/0192308 A1     8/2006     Juni
2007/0007455 A1     1/2007     Juni

FOREIGN PATENT DOCUMENTS

| WO | WO 04/072679 | 8/2004 |
|----|--------------|--------|
| WO | WO 05/006977 | 1/2005 |
| WO | WO 05/052634 | 6/2005 |
| WO | WO 06/029163 | 3/2006 |
| WO | WO 06/050845 | 3/2006 |
| WO | WO 06/065441 | 6/2006 |

OTHER PUBLICATIONS

De Kuhl, RQ Edwards and AR Ricci, The Mark III Scanner: A Compact Device for Multiple-View and Section Scanning of the Brain, Radiology, 1970, vol. 96, pp. 563-570.

De Kuhl, RQ Edwards, AR Ricci, RJ Yacob, TJ Mich and A Alavi, The Mark IV System for Radionuclide Computed Tomography of the Brain Radiology, 1976, vol. 121, pp. 405-413.

GF Knoll and JJ Williams, Application of a Ring Pseudorandom Aperture for Transverse Section Tomography, IEEE Transactions on Nuclear Science, 1977, vol. NS-24, pp. 581-586.

JJ Williams, WP Snapp and GF Knoll, Introducing SPRINT: A single Photon Ring System for Emission Tomography, IEEE Transactions on Nuclear Science, 1979, vol. NS-26, pp. 628-633.

M Tanaka, Y Hirose, K Koga and H Hattori, Engineering Aspects of a Hybrid Emission Computed Tomograph, IEEE Transactions on Nuclear Science, 1981, vol. NS-28, pp. 137-141.

WL Rogers, NH Clinthorne, J Stamos, KF Koral, R Mayans, JW Keyes, Jr., JJ Williams, WP Snapp and GF Knoll, SPRINT: A Stationary Detector Single Photon Ring Tomograph for Brain Imaging, IEEE Transactions on Medical Imaging, 1982, vol. MI-1, pp. 63-68.

Y Hirose, Y Ikeda, Y Higashi, K Koga, H. Hattori, I Kanno, Y Miura, S Miura and K Uemura, A Hybrid Emission CT, IEEE Transactions on Nuclear Science, 1982, vol. NS-29, pp. 520,523.

GF Knoll, Single-Photon Emission Computed Tomography, IEEE Proc., 1983, vol. 71, pp. 320-332.

WL Rogers, NH Clinthorne, J Stamos, KF Koral, R Mayans, FG Knoll J Juni, JW Keyes, Jr. and BA Harkness, Performance Evaluation of SPRINT, A Single Photon Ring Tomograph for Brain Imaging, J. Nucl. Med., 1984, vol. 25, pp. 1013-1018.

WL Rogers, NH Clinthorne, L. Shao, P Chiao, Y Ding, JA Stamos and KF Koral, SPRINT II: A Second Generation Single Photon Ring Tomograph, IEEE Transactions on Medical Imaging, 1988, vol. 7, pp. 291-297.

GL Zeng, Q Huang, Q Tang and WJ Wright, Skew-Slit Collimator for Small Animal SPECT, Society of Nuclear Medicine, Jun. 7, 2006, Oral Presentation, Abstract #664.

JW Hugg, E Asma, J Uribe, FP Jansen, RM Manjeshwar, H Lai, JC Paing, JR Dubois and X Guo, A Small-Animal SPECT/CT System for Dynamic Preclinical Imaging, Dynamic Nuclear Medicine Workshop: Oral Presentation, Abstract Banff International Research Station, Mar. 28, 2006.

JW Hugg, FP Jansen, J Uribe, RM Manjeshwar, H Lai, JC Pang and X Guo, A Small Animal SPECT/CT System with a Stationary CZT Detector Ring and Rotating Multiple Slit or Pinhole Collimator, Oral Presentation, Abstract M13-4, IEEE Medical Imaging Conference, San Diego, Nov. 4, 2006.

JW Hugg, FP Jansen, J Uribe, RM Manjeshwar, H. Lai, JC Pang and X Guo, Design of a Small-Animal SPECT System with a Stationary CZT Detector Ring, Oral Presentation, Abstract MR01-4, IEEE/Room Temperature Semiconductor Detector Conference, San Diego, Nov. 1, 2006.

JW Hugg, FP Jansen, J Uribe and RM Manjeshwar, Design of Multi-Slit and Multi-Pinhole Collimators for a Small-Animal SPECT System with a Stationary CZT Detector Ring, Poster Abstract M06-26, IEEE Medical Imaging Conference, San Diego, Nov. 2, 2006.

J Hugg, J Uribe, F Jansen, R Manjeshwar, H Lai, J Pang, J Dubois and X Guo, Small-Animal SPECT/CT Pre-Clinical Imaging System, Poster Abstract 168, Academy of Molecular Imaging Orlando, Mar. 25, 2006.

JW Hugg, J Uribe, FP Jansen, RM Manjeshwar, H Lai, JC Pang, JR Dubois and X Guo, A Small-Animal MicroSPECT/MicroCT System with a Stationary CZT Detector Ring and Rotating Multi-Pinhole and Multi-Slit Collimators, Oral Presentation, Abstract 663, Society of Nuclear Medicine, San Diego, Jun. 7, 2006.

JW Hugg, FP Jansen, J Uribe, RM Manjeshwar, JC Pang, H Lai and X Guo, A Small-Animal SPECT/CT System with Stationary CZT Detector Ring for Dynamic Preclinical Imaging, Poster Abstract 782, Society of Molecular Imaging, Honolulu, Sep. 2, 2006.

JW Hugg, J Uribe, FP Jansen, RM Manjeshwar, H Lai, JC Pang, JR Dubois and X Guo, A Small Animal SPECT/CT System with a Stationary CZT Detector Ring and Rotating Multi-Pinhole and Multi-Slit Collimators, Oral Presentation and Abstract, Workshop on Small-Animal SPECT, University of Arizona, Tucson, Mar. 9, 2006.

* cited by examiner

COMBINED SLIT/PINHOLE COLLIMATOR METHOD AND SYSTEM

BACKGROUND

The invention relates generally to non-invasive imaging such as single photon emission computed tomography (SPECT) imaging. More particularly, the invention relates to combined slit/pinhole collimators for use in non-invasive imaging.

SPECT is used for a wide variety of imaging applications, such as medical imaging. In general, SPECT systems are imaging systems that are configured to generate an image based upon the impact of photons (generated by a nuclear decay event) against a gamma-ray detector. In medical and research contexts, these detected photons may be processed to formulate an image of organs or tissues beneath the skin.

To produce an image, one or more detector assemblies may be rotated around a subject. Detector assemblies are typically comprised of various structures working together to receive and process the incoming photons. For instance, the detector assembly may utilize a scintillator assembly (e.g., large sodium iodide scintillator plates) to convert the photons into light for detection by an optical sensor. This scintillator assembly may be coupled by a light guide to multiple photomultiplier tubes (PMTs) or other light sensors that convert the light from the scintillator assembly into an electric signal. In addition to the scintillator assembly-PMT combination, pixilated solid-state direct conversion detectors (e.g., CZT) may also be used to generate electric signals from the impact of the photons. This electric signal can be easily transferred, converted, and processed by electronic modules in a data acquisition module to facilitate viewing and manipulation by clinicians.

Typically, SPECT systems further include a collimator assembly that may be attached to the front of the gamma-ray detector. In general, the collimator assembly is designed to absorb photons such that only photons traveling in certain directions impact the detector assembly. For example, multi-hole collimators comprised of multiple, small-diameter channels separated by lead septa have been used. With these multi-hole collimators, photons that are not traveling through the channels in a direction generally parallel to the lead septa are absorbed. In addition, while parallel-hole collimators are typically used, collimators also may have converging holes for image magnification or diverging holes for minifying the image. For improved resolution, a pinhole collimator may be used. Pinhole collimators are generally collimators with one or more small pinhole apertures therein. By way of example, an improved image resolution may be obtained with a pinhole collimator, e.g., if the subject is closer to the pinhole than the pinhole is to the gamma-ray detector.

While current SPECT systems have been used successfully, these systems have a number of disadvantages. For instance, rotation of the gamma-ray detectors along with the corresponding collimator assemblies around the subject typically requires large and expensive positioning systems capable of rotating the equipment with the needed precision. In addition, extended examination times are typically required because the detector assemblies must be rotated around the subject to obtain images from multiple angles around the subject. Moreover, current systems also do not provide the desired resolution and sensitivity. By way of example, the sensitivity of SPECT systems with multi-hole collimators may be reduced because only photons traveling in a direction generally parallel to the axis of the holes pass through the collimator. For similar reasons, SPECT systems with multi-hole collimators also may not provide the desired positional resolution.

Accordingly, it would be desirable to provide an imaging system with improved positional resolution and sensitivity while also having reduced examination times and simpler positioning systems.

BRIEF DESCRIPTION

In accordance with one embodiment, the present technique provides a collimator assembly. The collimator assembly includes an inner combined collimator and an outer collimator. The inner combined collimator includes a first portion having one or more slit apertures therein, and a second portion having one or more pinhole apertures therein. The outer collimator includes one or more septa spaced on a side of the first portion of the inner combined collimator. The slit apertures of the inner combined collimator and the septa of the outer collimator are arranged to define a plurality of apertures through the collimator assembly.

In accordance with another embodiment, the present technique provides an imaging system. The imaging system includes a collimator assembly and a detector array. The collimator assembly includes an inner combined collimator and an outer collimator. The inner combined collimator includes a first portion having one or more slit apertures therein and a second portion having one or more pinhole apertures therein. The outer collimator includes one or more septa spaced on a side of the first portion of the inner combined collimator opposite from a field of view. The slit apertures of the inner combined collimator and the septa of the outer collimator are arranged to define a plurality of apertures through the collimator assembly. The detector assembly is configured to detect gamma rays emanating from the field of view that pass through the collimator assembly and to generate one or more signals in response to the detected gamma rays.

In accordance with yet another embodiment, the present technique provides a method of imaging a volume. The method includes positioning at least a portion of a subject in a field of view of a SPECT system. The method further includes collimating gamma rays emitted from the portion of the subject using a collimator assembly that includes an inner combined collimator and an outer collimator. The inner combined collimator includes a first portion having one or more slit apertures therein, and a second portion having one or more pinhole apertures therein. The outer collimator includes one or more septa spaced on a side of the first portion of the inner combined collimator opposite from the field of view. The slit apertures of the inner combined collimator and the septa of the outer collimator define one or more pathways through the collimator assembly. Gamma rays aligned with one of the pinhole apertures, and gamma rays aligned with one of the slit/septa pathways pass through the collimator assembly. The collimator assembly absorbs gamma rays not aligned with one of the pinhole apertures or one of the slit/septa pathways. The method further includes detecting the gamma rays that pass through the collimator assembly, and generating one or more signals in response to the detected gamma rays.

DRAWINGS

These and other features, aspects, and advantages of the present invention will become better understood when the following detailed description is read with reference to the accompanying drawings in which like characters represent like parts throughout the drawings, wherein.

DETAILED DESCRIPTION

Figure 1:
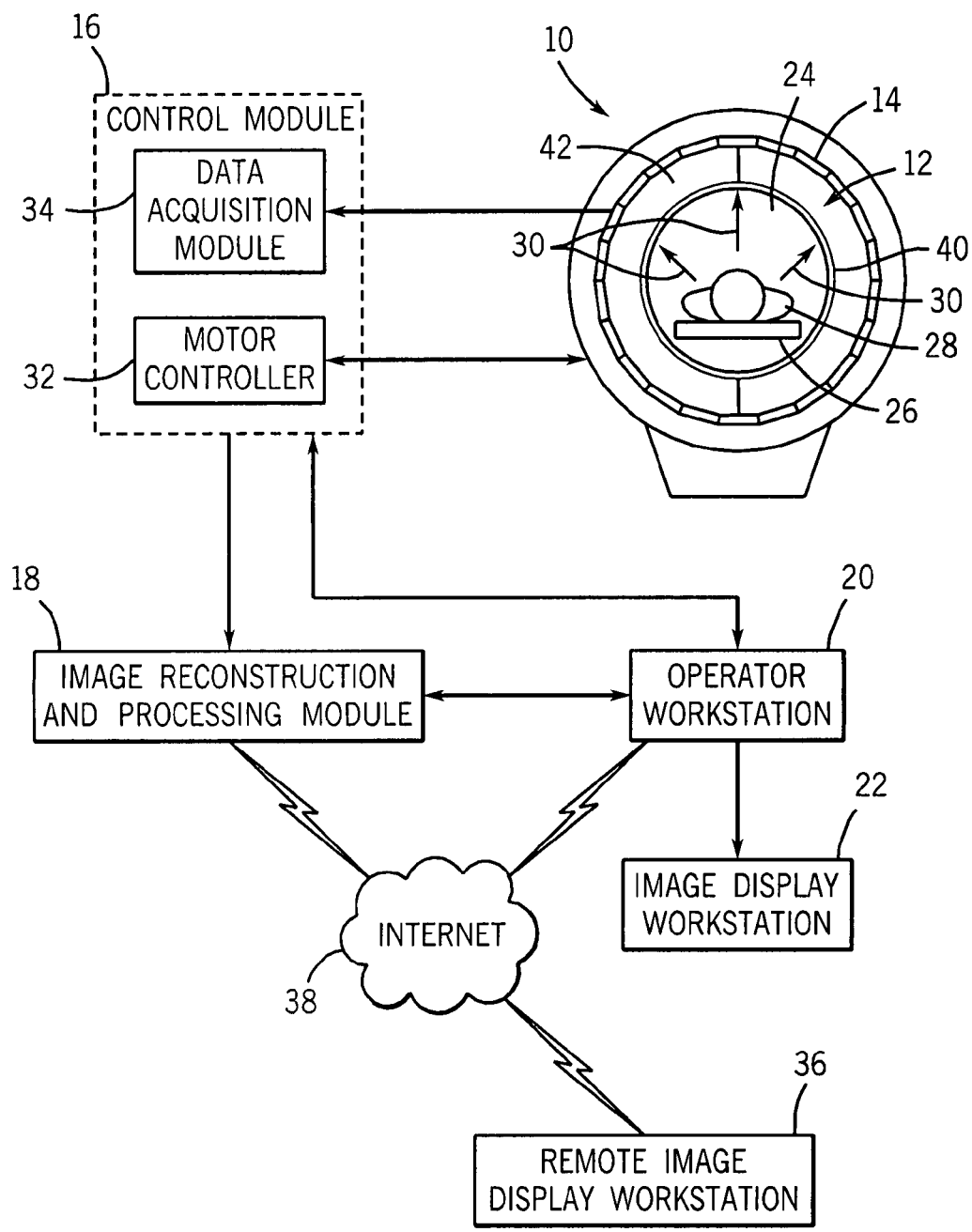
FIG. 1 is an illustration of an exemplary SPECT system which may include a collimator assembly in accordance with embodiments of the present technique.

FIG. 1 illustrates an exemplary SPECT system 10 for acquiring and processing image data in accordance with exemplary embodiments of the present technique. In the illustrated embodiment, SPECT system 10 includes a collimator assembly 12 and a detector assembly 14. The SPECT system 10 also includes a control module 16, an image reconstruction and processing module 18, an operator workstation 20, and an image display workstation 22. Each of the aforementioned components will be discussed in greater detail in the sections that follow.

SPECT system 10 also includes a field of view 24 into which a subject support 26 (e.g. a table) may be positioned for supporting a subject 28 (e.g., a human patient, a small animal, a plant, a porous object, etc.) in a generally stationary position for scanning. Alternatively, the subject support 26 may be stationary, while the SPECT system 10 may be positioned around the subject 28 for scanning. Those of ordinary skill in the art will appreciate that the subject 28 may be positioned in any suitable position for scanning. By way of example, the subject 28 may be positioned in the field of view 24 in a generally vertical position, a generally horizontal position, or any other suitable position for the desired scan. In SPECT imaging, the subject 28 is typically injected with a solution that contains a radioactive tracer. The solution is distributed and absorbed throughout the subject 28 in different degrees, depending on the tracer employed and, in the case of living subjects, the functioning of the organs and tissues. The radioactive tracer emits electromagnetic rays 30 (e.g., photons or gamma quanta) known as "gamma rays" during a nuclear decay event.

As previously mentioned, the SPECT system 10 includes the collimator assembly 12 that receives the gamma rays 30 emanating from the subject 28 in the field of view 24. As will be described below, the collimator assembly 12 is generally configured to limit and define the direction and angular divergence of the gamma rays 30. In general, the collimator assembly 12 is disposed between the detector assembly 14 and the field of view 24. In accordance with exemplary embodiments of the present technique, the collimator assembly 12 includes an outer collimator 42 and an inner combined collimator 40 having a slitted portion and a pinhole aperture portion. In general, the inner and outer collimators 40, 42 may contain a radiation absorbent material, such as lead or tungsten, for example. As will be discussed in more detail below with respect to FIG. 2, inner combined collimator 40 generally contains a slitted portion 48 having one or more slit apertures 44a-44e therein and a pinhole aperture portion 50 having one or more pinhole apertures 46 therein. In addition, the outer collimator 42 generally includes one or more septa 58 spaced on a side of the slitted portion 48 of the inner combined collimator 40 opposite from the field of view 24. Referring again to FIG. 1, the collimator assembly 12 extends at least partially around the field of view 24. In exemplary embodiments, the collimator assembly 12 may extend up to about 360° around the field of view 24. By way of example, the collimator assembly 12 may extend from about 180° to about 360° around the field of view 24.

The gamma rays 30 that pass through the collimator assembly 12 impact the detector assembly 14. Due to the collimation of the gamma rays 30 by the collimator assembly 12, the detection of the gamma rays 30 may be used to determine the line of response along which each of the gamma rays 30 traveled before impacting the detector assembly 14, allowing localization of each gamma ray's origin to that line. In general, the detector assembly 14 includes a plurality of detector elements configured to detect the gamma rays 30 emanating from the subject 28 in the field of view 24 and passing through one or more apertures defined by the collimator assembly 12. In exemplary embodiments, each of the plurality of detector elements in the detector assembly 14 produces an electrical signal in response to the impact of the gamma rays 30.

As will be appreciated by those of ordinary skill in the art, the detector elements of the detector assembly 14 may include any of a variety of suitable materials and/or circuits for detecting the impact of the gamma rays 30. By way of example, the detector elements may include a plurality of solid-state detector elements, which may be provided as one-dimensional or two-dimensional arrays. In another embodiment, the detector elements of the detector assembly 14 may include a scintillation assembly and PMTs or other light sensors.

Moreover, the detector elements may be arranged in the detector assembly 14 in any suitable manner. By way of example, the detector assembly 14 may extend at least partially around the field of view 24. In certain embodiments, the detector assembly 14 may include modular detector elements arranged around the field of view 24. Alternatively, the detector assembly 14 may be arranged in a ring that may extend up to about 360° around the field of view 24. In certain exemplary embodiments, the detector assembly 14 may extend from about 180° to about 360° around the field of view 24. The ring of detector elements may include flat panels or curved detector surfaces (e.g., a NaI annulus). In one exemplary embodiment, the ring may comprise in the range from 9-10 solid-state detector panels with each detector panel comprising four detector modules. Those of ordinary skill in the art will appreciate that the ring need not be circular, for example, the detector elements may be arranged in an elliptical ring or be contoured to the body profile of the subject 28. In addition, in certain exemplary embodiments, the detector assembly 14 may be gimbaled on its support base, e.g., so that arbitrary slice angles may be acquired.

To acquire multiple lines of response emanating from the subject 28 in the field of view 24 during a scan, the collimator assembly 12 may be configured to rotate about the subject 28 positioned within the field of view 24. In accordance with exemplary embodiments, the collimator assembly 12 may be configured to rotate with respect to the detector assembly 14. By way of example, the detector assembly 14 may be stationary while the collimator assembly 12 may be configured to rotate about the field of view 24. Alternatively, the detector assembly 14 may rotate while the collimator assembly 12 is stationary. In certain exemplary embodiments, the collimator assembly 12 and the detector assembly 14 may both be configured to rotate, either together or independent of one another. As will be discussed in more detail below, the outer collimator 42 should co-rotate with the slitted portion of the inner combined collimator 40, in accordance with exemplary embodiments of the present technique. Alternatively, if sufficient pinhole apertures and slit apertures are provided in the inner combined collimator 40, then no rotation may be required. Also, if the slit apertures are orthogonal to the longitudinal axis of the collimator assembly 12 (as illustrated below with respect to FIG. 4), then no rotation may be required.

SPECT system 10 further includes a control module 16. In the illustrated embodiment, the control module 16 includes a motor controller 32 and a data acquisition module 34. In general, the motor controller 32 may control the rotational speed and position of the collimator assembly 12, the detector assembly 14, and/or the position of the subject support 26. The data acquisition module 34 is configured to obtain the signals generated in response to the impact of the gamma rays 30 with the detector assembly 14. For example, the data acquisition module 34 may receive sampled electrical signals from the detector assembly 14 and convert the data to digital signals for subsequent processing by an image reconstruction and processing module 18.

Those of ordinary skill in the art will appreciate that any suitable technique for data acquisition may be used with SPECT system 10. By way of example, the data needed for image reconstruction may be acquired in a list or a frame mode.

In one exemplary embodiment of the present technique, gamma ray events (e.g., the impact of gamma rays 30 on the detector assembly 14), gantry motion (e.g., collimator assembly 12 motion and subject support 26 position), and physiological signals (e.g., heart beat and respiration) may be acquired in a list mode. For example, a time-stamp may be associated with each gamma ray event (e.g., energy and position) or by interspersing regular time stamps (e.g., every 1 ms) into the list of gamma ray events. The physiological signals may be included in the list, for example, when they change by a defined amount or with every regular time stamp. In addition, gantry motion may also be included in the event lists, for example, when it changes by a defined amount or with every regular time stamp. The list mode data may be binned by time, gantry motion or physiological gates before reconstruction. List mode may be suitable in exemplary embodiments where the count rate is relatively low and many pixels record no counts at each gantry position or physiological gate.

Alternatively, frames and physiological gates may be acquired by moving the gantry in a step-and-shoot manner and storing the number of events in each pixel during each frame time and heart or respiration cycle phase. Frame mode may be suitable, for example, where the count rate is relatively high and most pixels are recording counts at each gantry position or physiological gate.

In the illustrated embodiment, the image reconstruction and processing module 18 is coupled to the data acquisition module 34. The signals acquired by the data acquisition module 34 are provided to the image reconstruction and processing module 18 for image reconstruction. The image reconstruction and processing module 34 may include electronic circuitry to provide the drive signals, electronic circuitry to receive acquired signals, and electronic circuitry to condition the acquired signals. Further, the image reconstruction and processing module 34 may include processing to coordinate functions of the SPECT system 10, to implement reconstruction algorithms suitable for reconstruction of the acquired signals. The image reconstruction and processing module 34 may include a digital signal process, memory, a central processing unit (CPU) or the like, for processing the acquired signals. As will be appreciated, the processing may include the use of one or more computers within the image reconstruction and processing module 34. The addition of a separate CPU may provide additional functions for image reconstruction, including, but not limited to, signal processing of data received, and transmission of data to the operator workstation 20 and image display workstation 22. In one embodiment, the CPU may be confined within the image reconstruction and processing module 34, while in another embodiment a CPU may include a stand-alone device that is separate from the image reconstruction and processing module 34.

The reconstructed image may be provided to the operator workstation 20. The operator workstation 20 may be utilized by a system operator to provide control instructions to some or all of the described components and for configuring the various operating parameters that aid in data acquisition and image generation. An image display workstation 22 coupled to the operator workstation 20 may be utilized to observe the reconstructed image. It should be further noted that the operator workstation 20 and the image display workstation 22 may be coupled to other output devices, which may include printers and standard or special purpose computer monitors. In general, displays, printers, workstations, and similar devices supplied with the SPECT system 10 may be local to the data acquisition components, or may be remote from these components, such as elsewhere within the institution or hospital, or in an entirely different location, linked to the image acquisition system via one or more configurable networks, such as the Internet, virtual private networks, and so forth. By way of example, the operator workstation 20 and/or the image reconstruction and processing module 18 may be coupled to a remote image display workstation 36 via a network (represented on FIG. 1 as Internet 38).

Furthermore, those of ordinary skill in the art will appreciate that any suitable technique for image reconstruction may be used with the SPECT system 10. In one exemplary embodiment, iterative reconstruction (e.g., ordered subsets expectation maximization, OSEM) may be used. Iterative reconstruction may be suitable for certain implementations of the SPECT system 10 due, for example, to its speed and the ability to tradeoff reconstruction resolution and noise by varying the convergence and number of iterations.

While in the illustrated embodiment, the control module 16 (including the data acquisition module 34 and the motor controller 32) and the image reconstruction and processing module 18 are shown as being outside the detector assembly 14 and the operator workstation 20. In certain other implementations, some or all of these components may be provided as part of the detector assembly 14, the operator workstation 20, and/or other components of the SPECT system 10.

Figure 2:
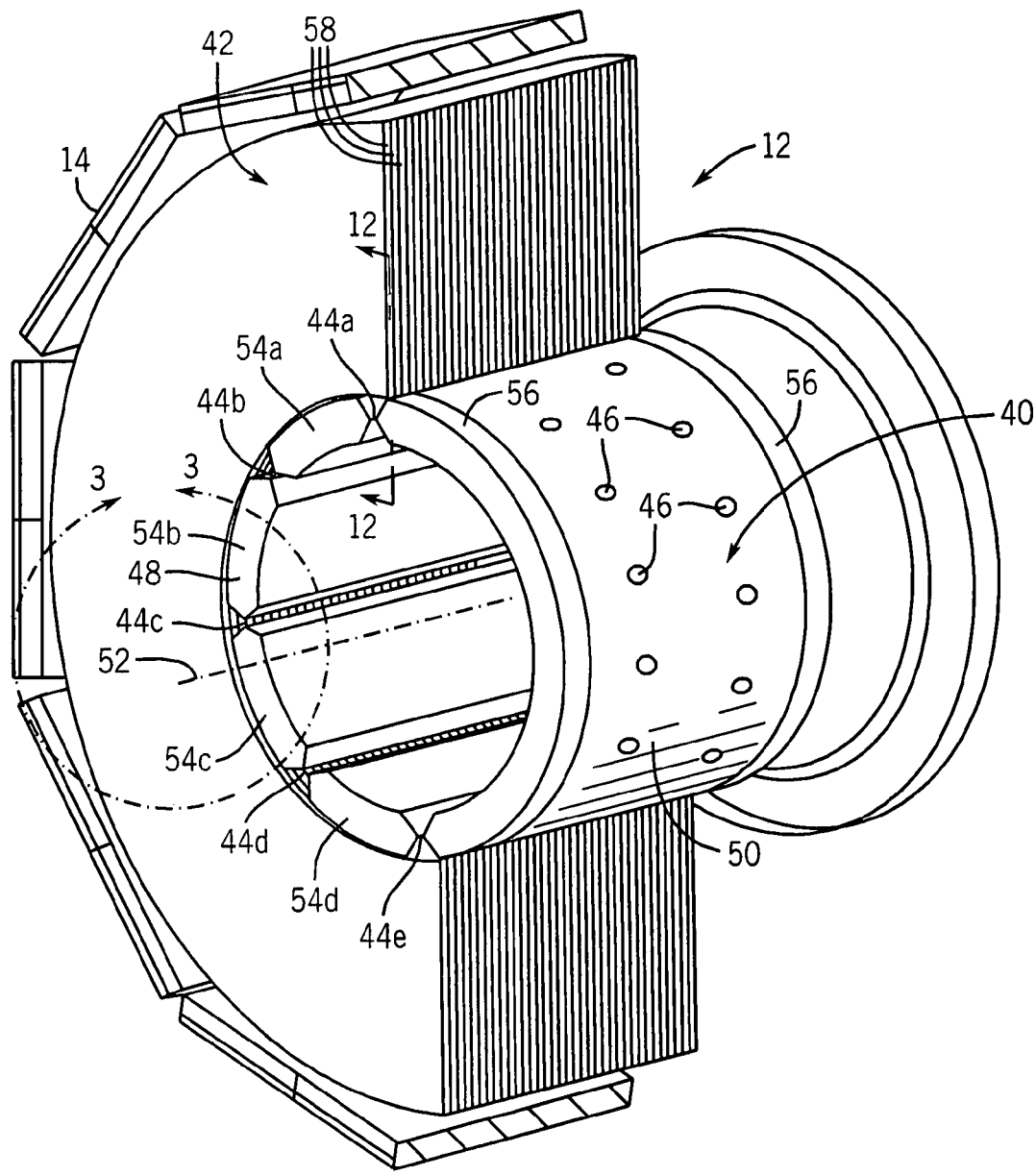
FIG. 2 is a perspective view of an exemplary collimator assembly that includes an inner combined collimator having a slitted portion and a pinhole aperture portion, in accordance with embodiments of the present technique.

Those of ordinary skill in the art will appreciate that pinhole collimators may be advantageously used for small field of view imaging. In certain embodiments, when using a pinhole collimator multiple images may be formed with the subject at different positions within the field of view to form a composite whole-body image. However, this technique will generally require more time to acquire than a whole-body image obtained with a slit collimator. Accordingly, embodiments of the present technique provide a collimator assembly 12 that includes inner combined collimator 40 having a slitted portion 48 and a pinhole aperture portion 50, as illustrated in FIG. 2. By way of example, the pinhole apertures 46 (commonly referred to simply as pinholes) in the pinhole aperture portion 50 may be focused on a small field of view while the slit apertures 44a-44e in the slitted portion 48 may be focused on a larger, usually overlapping field of view. By focusing the slit apertures 44a-44e and the pinhole apertures 46 on different fields of view, activity outside the small field of view should properly imaged and, thus, not be aliased into the small field of view during reconstruction. Also, the slit and pinhole apertures may provide complementary information about the distribution of a radiopharmaceutical tracer in various body tissues. By way of example, in a subject suspected of having cancer in a particular organ, the pinhole apertures 46 could be focused on the target organ while the slit apertures 44a-44e could be focused on a large field of view in order to screen for metastatic tumors. Furthermore, the slit and pinhole apertures may have different spatial resolutions and sensitivities. By way of example, the image reconstruction quality may be improved by properly accounting for the combination of higher spatial resolution data over a small field of view and lower spatial resolution data over a larger field of view.

In the embodiment illustrated in FIG. 2, a perspective view of the collimator assembly 12 with a detector assembly 14 encircling the collimator assembly 12 is illustrated, in accordance with exemplary embodiments of the present technique. As illustrated, a portion of the detector assembly 14 is removed to illustrate the components of the collimator assembly 12, particularly the pinhole aperture portion 50 and the one or more septa 58. As previously described with respect to FIG. 1, the collimator assembly 12 includes an inner combined collimator 40 proximate to a volume (e.g., the field of view 24 illustrated on FIG. 1) and an outer collimator 42. The inner combined collimator 40 includes a slitted portion 40 having one or more slit apertures 44a-44e therein and a pinhole aperture portion 50 having one or more pinhole apertures 46 therein. The outer collimator 42 includes one or more septa 58, spaced on a side of the slitted portion 48 of the inner combined collimator 40 opposite from the field of view 24.

As will be discussed in more detail below, the collimator assembly 12 may be arranged such that gamma rays aligned with one of the pathways defined by the slit apertures 44a-44e in the slitted portion 48 of the inner combined collimator 40 and the spaced septa 58 of the outer collimator 42 should pass through the collimator assembly 12. In the illustrated embodiment, the slit apertures 44a-44e provide longitudinal information, and the septa 58 provide the transaxial slice definition. In addition, the collimator assembly 12 may be arranged such that gamma rays aligned with one of the pinhole apertures 46 in the inner combined collimator 40 should pass through the collimator assembly. However, the collimator assembly 12 may be arranged such that the collimator assembly 12 should absorb gamma rays that are not aligned with either the slit/septa pathways or the pinhole apertures 46.

As previously mentioned, the inner combined collimator 40 includes a slitted portion 48 having one or more slit apertures 44a-44e therein and a pinhole aperture portion 50 having one or more pinhole apertures 46 therein. As illustrated, the slit apertures 44a-44e may extend in a direction generally parallel to the longitudinal axis 52 of the inner combined collimator 40. In addition, the slitted portion 48 of the inner combined collimator 40 may include one or more sections spaced around the longitudinal axis 52 of the inner combined collimator 40 such that spaces between the sections define the slit apertures 44a-44e. By way of example, the spaced sections may be or include one or more panels 54a-54d spaced around the longitudinal axis 52 of the inner combined collimator 40 so as to define the slit apertures 44a-44e. The slit apertures 44a and 44e at the respective ends of the slitted portion 48 may be defined by the spaces between the each of the panels 54a and 54d and the pinhole aperture portion 50.

The pinhole aperture portion 50 of the inner combined collimator contains one or more pinhole apertures 46 therein. In the illustrated embodiment, the pinhole apertures 46 in the pinhole aperture portion 50 are arranged in two staggered rows. Additionally, while the slit apertures 44a-44e are generally one-dimensional, the pinhole apertures 46 in the pinhole aperture portion 50 are generally two-dimensional. The slit apertures 44a-44e are referred to as generally one dimensional because the length of a slit aperture 44 is typically long in comparison to the width of the slit aperture 44. For example, the length of a slit aperture 44 may be four, five, ten, or more times greater than the respective width of the slit aperture 44. Conversely, the pinhole apertures 46 may have lengths and widths that are generally comparable to one another. For example, the pinhole apertures 46 may have a length that is generally no more than two or three times greater than the respective widths. Often the pinhole apertures 46 may be circular, square, or hexagonal. Such pinhole apertures 46 in the pinhole aperture portion 50 are commonly referred to as "pinholes." Additionally, the slit apertures 44a-44e in combination with the septa 58 generally define a two-dimensional fan-beam imaging geometry, while the pinhole apertures 46 generally define a three-dimensional cone-beam imaging geometry.

For support, the panels 54a-54d and the pinhole aperture portion 50 may be coupled by a mechanical coupling mechanism, such as bands (rings) 56 illustrated in FIG. 2. By way of example, each of the bands 56 may be coupled to each of the panels 54a-54d and the pinhole aperture portion 50 at the respective ends of the collimator assembly 12. As illustrated, the bands 56 may be configured to hold the panels 54a-54d and the pinhole aperture portion 50 in a generally cylindrical arrangement. Further, while the panels 54a-54d and the pinhole aperture portion 50 are illustrated in FIG. 2 as curved sections, the present technique encompasses the use of sections that are not curved. In addition, while the pinhole aperture portion 50 and the panels 54a-54d of the slitted portion 48 are illustrated as separate sections, the present technique encompasses the use of a unitary inner combined collimator 40. That is, the inner combined collimator 40 may be fabricated as a solid piece having one or more slit apertures 44a-44e and pinhole apertures 46 therein. The inner combined collimator 40 may also be constructed as a unitary piece in which the slit apertures 44a-44e and pinhole apertures 46 are filled by a material that provides mechanical support but that also allows most gamma rays to pass through the slit apertures 44a-44e and/or pinhole apertures 46 without interaction. While the preceding discussion has described the inner combined collimator 40 as having a single slitted aperture portion 48 and a single pinhole aperture portion 50, one of ordinary skill in the art will recognize that the design may be extended to include multiple intermingled slitted and pinhole aperture portions. For each slitted aperture portion, a corresponding outer collimator 42 with spaced septa 58 would be placed to define slit/septa gamma ray pathways.

While the inner combined collimator 40 is illustrated as being generally cylindrically shaped, the present technique encompasses the employment of inner combined collimators that are not generally cylindrically shaped. By way of example, the inner combined collimators may each be or include a flat panel having a slitted portion 48 and a pinhole aperture portion 50. Furthermore, one of ordinary skill in the art will recognize that the collimators and detectors may be combined in modules and positioned to view portions of the field of view. If only a few collimator/detector modules are deployed, then they may be moved to a plurality of positions during image acquisition in order to acquire sufficient data for tomographic image reconstruction. Alternatively, if sufficient collimator/detector modules are deployed, then they may remain stationary during image acquisition and yet acquire sufficient data for tomographic image reconstruction.

In addition, the inner combined collimator 40 should have a thickness sufficient to absorb any gamma rays that do not pass through the slit apertures 44a-44e or pinhole apertures 46. By way of example, the inner combined collimator 40 may have a thickness in the range of from about 10 mm to about 30 mm. Those of ordinary skill will appreciate that the required thickness to absorb gamma rays depends upon the energy of the gamma rays and the material properties of the collimator assembly 12. Further, the thickness of the inner combined collimator 40 should provide adequate mechanical strength to support the weight of the collimators and to allow rotation without unpredictable shape distortion.

Those of ordinary skill in the art will appreciate that the resolution and sensitivity of the SPECT system 10 is based in part on the width of the slit apertures 44a-44e, the spacing of the septa 58, and the cross-sectional area of the pinhole apertures 46. In general, the slit apertures 44a-44e and septa 58 may have the same or different widths, with different widths providing different resolving power. By way of example, the slit apertures 44a-44e may have two or more different widths. In exemplary embodiments, each of the slit apertures 44a-44e may have a width in the range of from about 0.1 mm to about 10 mm, typically in the range of from about 1 mm to about 5 mm. In general, the pinhole apertures 46 may have the same or different cross-sectional areas. By way of example, the pinhole apertures 46 may have two or more different cross-sectional areas. In exemplary embodiments, each of the pinhole apertures 46 may have a width in the range of from about 0.1 mm to about 10 mm, typically in the range of from about 1 mm to about 5 mm. The various slit apertures 44a-44e and/or pinhole apertures 46 may have a distribution of various sizes, and thus differing spatial resolutions and sensitivities. The image reconstruction algorithm should appropriately model the system response of the various apertures.

Furthermore, those of ordinary skill in the art will appreciate that the efficiency of gamma ray detection is based on the number of slit apertures 44a-44e and pinhole apertures 46 in the inner combined collimator 40. By way of example, a collimator assembly 12 configured to have a large number of slit apertures 44a-44e and pinhole apertures 46 would typically require less or no rotation of the collimator assembly 12 to obtain a sufficient number of angular projections for image reconstruction. Accordingly, the number of slit apertures 44a-44e and pinhole apertures 46 may be adjusted to provide the desired imaging sensitivity for a desired imaging time. Those of ordinary skill in the art will appreciate that the number and spacing of the slit apertures 44a-44e and pinhole apertures 46 should be chosen with consideration of the efficient utilization of the detector assembly 14 and the performance of the image reconstruction and processing module 18. For example, limited overlap of gamma ray lines of response impacting on the detector assembly 14 may be acceptable.

As previously mentioned, the collimator assembly 12 further includes an outer collimator 42. In general, the outer collimator may include one or more septa 58 spaced on a side of the slitted portion 48 of the inner combined collimator 40 opposite from the field of view 24. In the illustrated embodiment, each of the septa 58 is generally arc-shaped and spaced along the longitudinal axis 52 of the collimator assembly 12. The septa 58 may be arranged, for example, to provide the desired slice information for the SPECT system 10. As illustrated, the septa 58 are generally parallel to each other and generally perpendicular to the longitudinal axis 52 of the collimator assembly 12. In this embodiment, the septa 58 may define the transaxial slice information for the SPECT system 10. Further, the outer collimator 42 and the inner combined collimator 40 may be mechanically coupled or placed in contact with each other, e.g., so as to rotate together. For example, in certain exemplary embodiments, the outer collimator 42 may co-rotate with the slitted portion 48 of the inner combined collimator 40.

Figure 3:
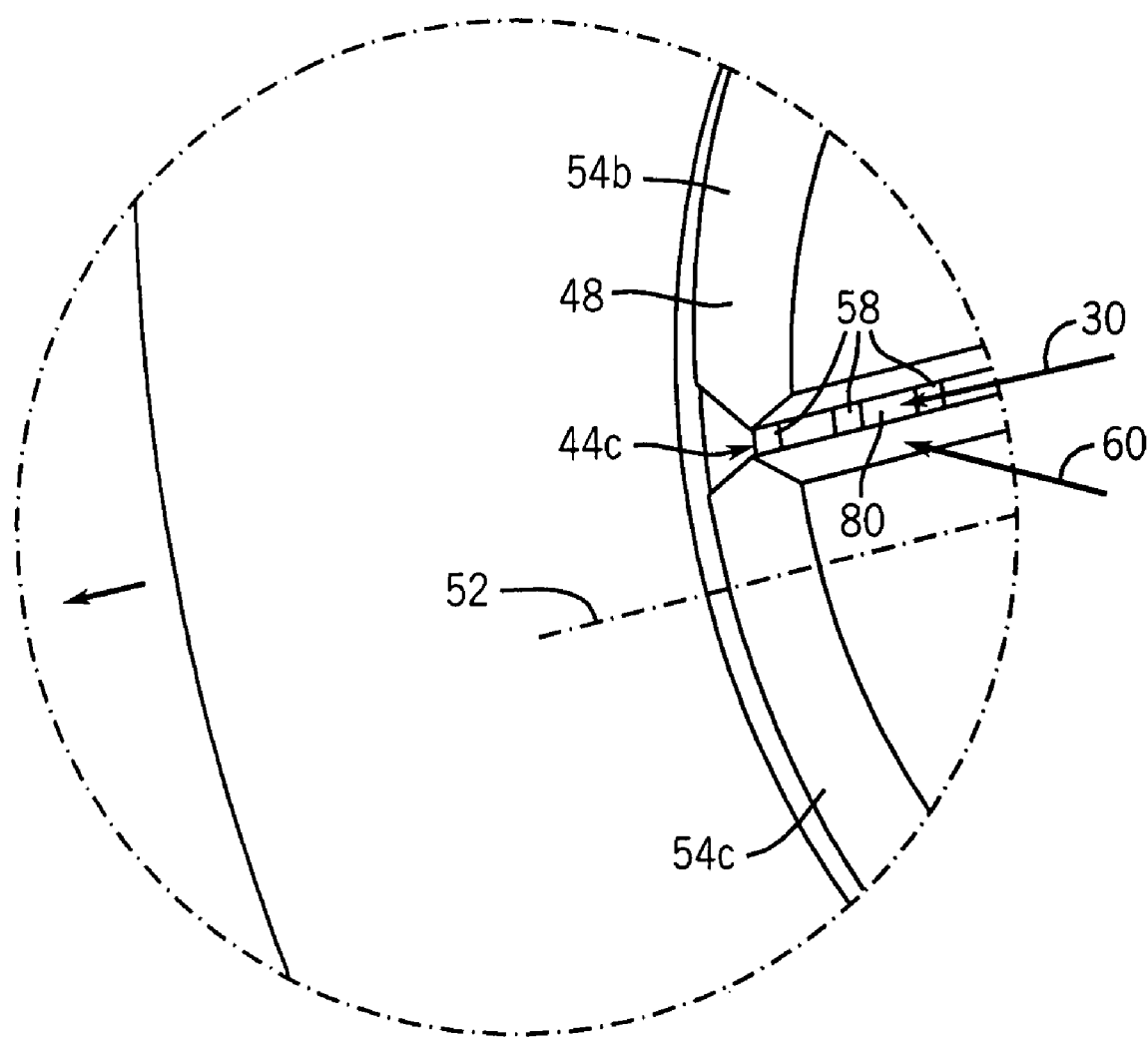
FIG. 3 is an enlarged view of the slitted portion of the exemplary collimator assembly of FIG. 2 taken along line 3-3, in accordance with embodiments of the present technique.

Referring now to FIG. 3, an enlarged view of the slitted portion 48 of the inner combined collimator 40 of FIG. 2 taken along line 3-3 is shown to illustrate how gamma rays pass through the slitted portion 48 of the collimator assembly 12. In the illustrated embodiment, the collimator assembly 12 is arranged such that septa 58 of the outer collimator 42 and the slit aperture 44c in the inner combined collimator 40 define gamma ray pathway 80 through the collimator assembly 12. As illustrated, gamma rays 30 aligned with this pathway 80 and traveling in a direction generally parallel to the septa 58 should pass through the collimator assembly 12. As such, gamma rays 30 emanating from subject 28 in the field of view 24 may pass through the collimator assembly 12 and impact the detector assembly 14. However, the collimator assembly 12 should absorb gamma rays that do not pass through a slit/septa gamma ray pathway. By way of example, the collimator assembly 12 should absorb gamma ray 60 that is not aligned with the pathway 80 and/or is not traveling in a direction generally parallel to the septa 58.

While the preceding discussion of FIGS. 2 and 3 has described the slitted portion 48 of the inner combined collimator 40 as having slit apertures 44a-44e extending in a direction generally parallel to the longitudinal axis 52 of the collimator assembly 12, and the outer collimator 42 as having septa 58 spaced along the longitudinal axis 52 of the collimator assembly, one of ordinary skill in the art will recognize that the present technique may be implemented with collimator assemblies having alternative slit configurations. For example, the slit apertures 44a-44e may extend in a direction generally perpendicular or generally diagonally to the longitudinal axis 52 of the collimator assembly 12.

Figure 4:
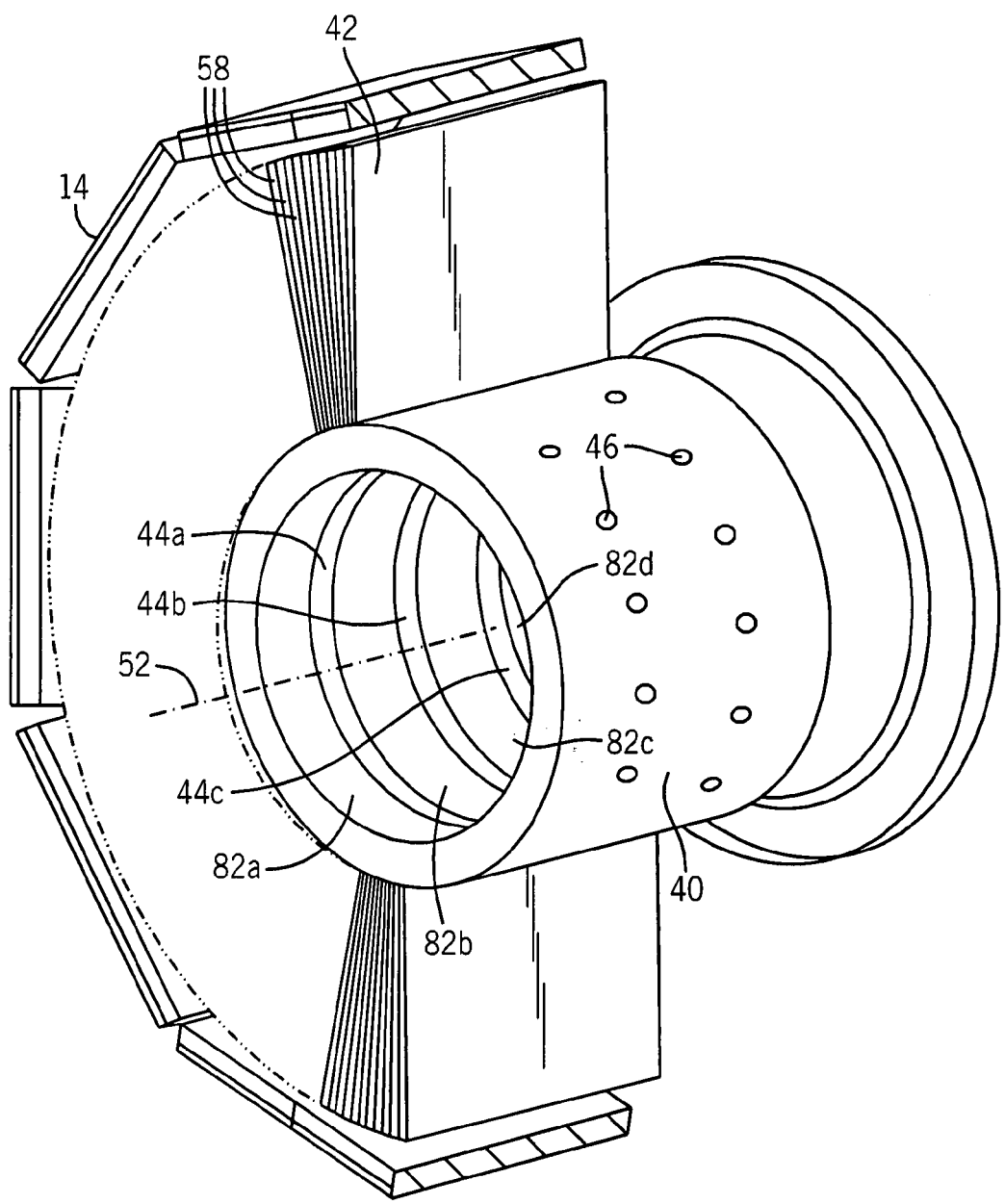
FIG. 4 is a perspective view of an alternative arrangement of an exemplary collimator that includes an inner combined collimator having a slitted portion and a pinhole aperture portion, in accordance with embodiments of the present technique.

By way of example, FIG. 4 illustrates a collimator assembly 12 that has an inner combined collimator 40 and an outer collimator 42 having an alternative slit configuration. As illustrated in FIG. 4, the slit apertures 44a-44c in the inner combined collimator 40 may extend in a direction generally perpendicular to the longitudinal axis 52 of the collimator assembly 12 while the septa 58 of the outer collimator 42 extend longitudinally and radially from the inner combined collimator 40. In the illustrated embodiment, the slitted portion 48 may include a plurality of sections spaced along the longitudinal axis 52 such that spaces between the sections define the slit apertures 44a-44c. By way of example, the spaced sections may include a plurality of cylindrical sections 82a-82d spaced along the longitudinal axis 52 so as to define the slit apertures 44a-44c. Further, in the illustrated embodiment, the slit apertures 44a-44c may provide the axial slice definition, and the septa may provide the in-slice (transaxial) information for the SPECT system 10.

Figure 5:
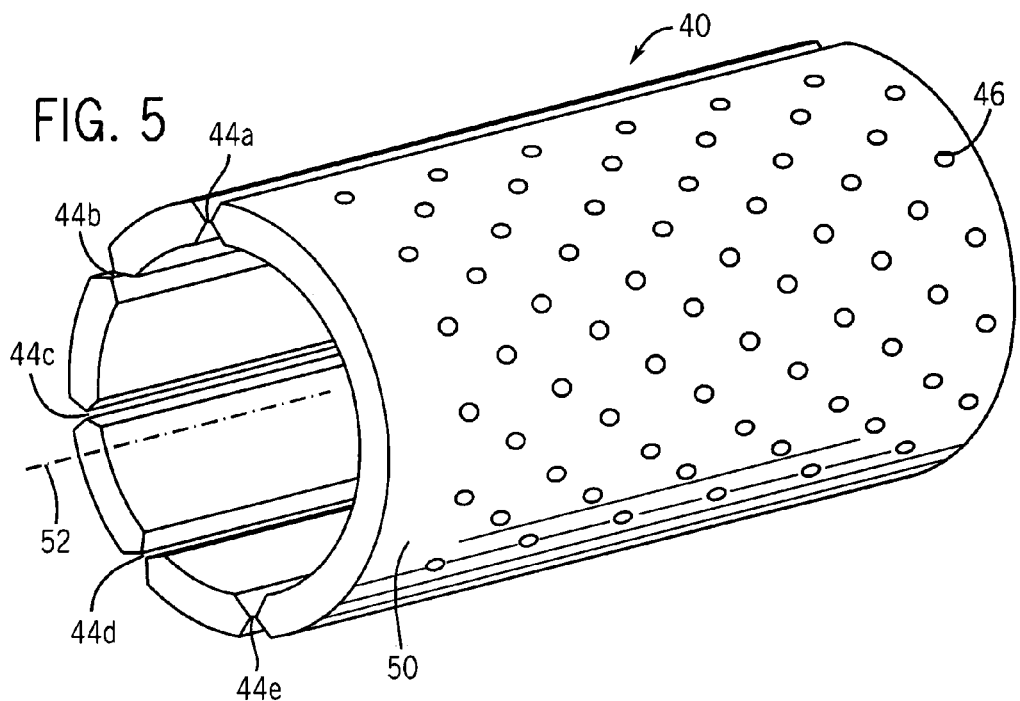
FIG. 5 is an illustration of another alternative arrangement of an exemplary collimator assembly that includes an inner combined collimator having a slitted portion and an aperture portion, in accordance with embodiments of the present technique.

Furthermore, while the preceding discussion, has described the pinhole aperture portion 50 of the inner combined collimator 40 as having two staggered rows of pinhole apertures 46 therein, those of ordinary skill in the art will recognize that the present technique may be implemented with collimator assemblies having alternative aperture configurations. By way of example, FIG. 5 illustrates a collimator assembly 12 that has inner combined collimator 40 with a pinhole aperture portion 50 having an alternative configuration. As illustrated in FIG. 5, the pinhole apertures 46 may be arranged in one or more rows or in any appropriate pattern, whether regular or pseudo-random. Those of ordinary skill in the art will appreciate that the number and spacing of the pinhole apertures 46 should be chosen with consideration of the efficient utilization of the detector assembly 14 and the performance of the image reconstruction and processing module 18. For example, limited overlap of gamma ray lines of response impacting on the detector assembly 14 may be acceptable. Furthermore, those of ordinary skill in the art will appreciate that the pinholes may point toward one or more fields of view which may be separate or may overlap.

Figure 6:
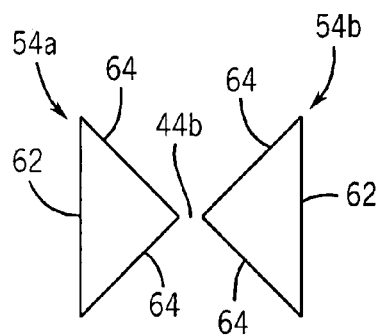
FIG. 6 is an illustration of an arrangement of one slit or pinhole aperture of an exemplary combined collimator in accordance with embodiments of the present technique.
Figure 7:
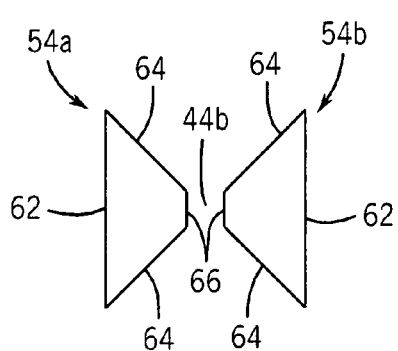
FIG. 7 is an illustration of an alternative arrangement of one slit or pinhole aperture of an exemplary combined collimator in accordance with embodiments of the present technique.
Figure 8:
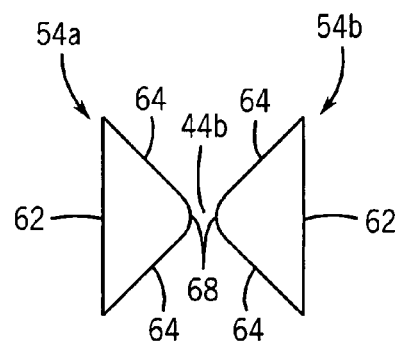
FIG. 8 is an illustration of another alternative arrangement of one slit or pinhole aperture of an exemplary combined collimator in accordance with embodiments of the present technique.

Referring now to FIGS. 6-8, the slitted portion 48 of the inner combined collimator 40 that defines slit aperture 44b is depicted as having different slit-edge configurations. Those of ordinary skill in the art will appreciate that varying the slit-edge configuration will generally impact the resolution, sensitivity, and field of view of the SPECT system 10. In exemplary embodiments, the slitted portion 48 may be configured as having slits edges that are sharp (e.g., knife-edge as in FIG. 6) or blunted (e.g., keel-edge as in FIG. 7, or round edge as in FIG. 8). Other slit edge configurations may also be suitable. Those of ordinary skill in the art will appreciate that the slit edge configuration may be selected based on, inter alia, the desired resolution, sensitivity, and field of view, including consideration of the performance of the image reconstruction and processing module 18. Further, the slit edges may be constructed from the same or different material as that used for the photon-absorbing collimator sections 54 or 50. Furthermore, those of ordinary skill in the art will appreciate that the pinhole apertures 46 of the pinhole aperture portion 50 of the inner combined collimator 40 can similarly have different aperture edges. FIGS. 6-8 can also depict pinhole aperture edges viewed in cross-section, although the labels refer to slit apertures.

FIG. 6 illustrates a cross-sectional, side view of one slit aperture 44b in the inner combined collimator 40 to illustrate the slit-edge configuration, in accordance with an embodiment of the present technique. As illustrated, slit aperture 44b is defined by the tips 62 of the cylindrical sections 54a and 54b of the slitted portion 48 of the inner combined collimator 40. In the illustrated embodiment, the tips 62 comprise angled segments 64 that define slit aperture 44b as having a knife-edge.

FIG. 7 illustrates a cross-sectional, side view of one slit aperture 44b in the inner combined collimator 40 to illustrate an alternative slit-edge configuration, in accordance with an embodiment of the present technique. As illustrated, slit aperture 44b is defined by the tips 62 of the cylindrical sections 54a and 54b of the slitted portion 48 of the inner combined collimator 40. In the illustrated embodiment, the tips 62 comprise angled segments 64 and blunt ends 66 that define slit aperture 44b as having a keel-edge.

FIG. 8 illustrates a cross-sectional, side view of one slit aperture 44b in the inner combined collimator 40 to illustrate another alternative slit-edge configuration, in accordance with an embodiment of the present technique. As illustrated, slit aperture 44b is defined by the tips 62 of the cylindrical sections 54a and 54b of the slitted portion 48 of the inner combined collimator 40. In the illustrated embodiment, the tips 62 comprise angled segments 64 and round ends 68 that define slit aperture 44b as having a round-edge.

Figure 9:
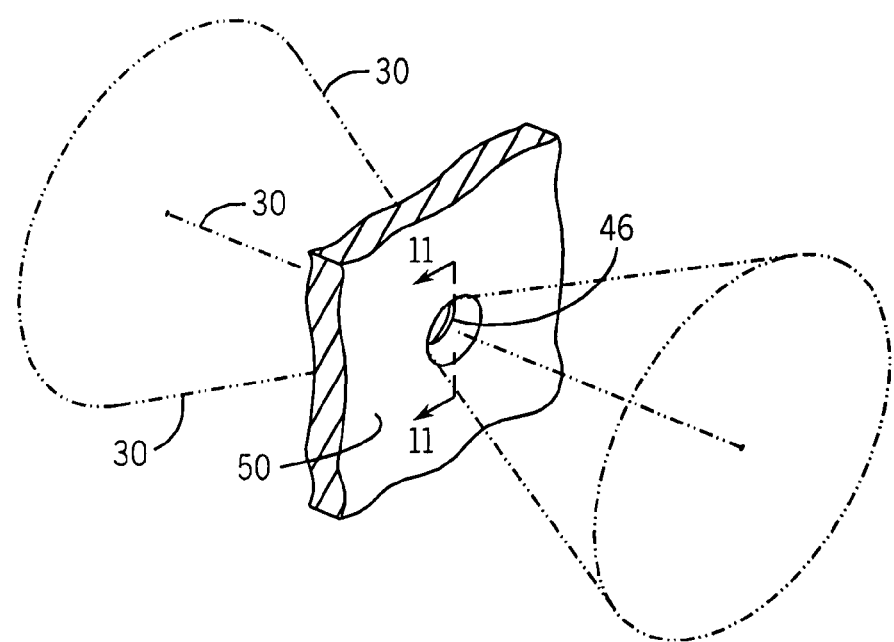
FIG. 9 is a perspective view of one pinhole aperture through an exemplary collimator assembly in accordance with embodiments of the present technique.
Figure 10:
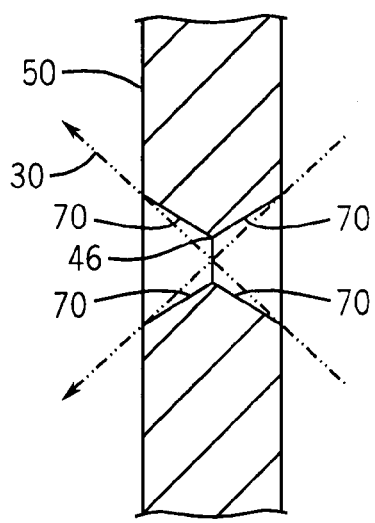
FIG. 10 is a cross-sectional view of the pinhole aperture portion of FIG. 9 taken along line 11-11, in accordance with embodiments of the present technique.

Referring now to FIGS. 9 and 10, a view of one pinhole aperture 46 through the collimator assembly 12 is illustrated. Only a portion of the collimator assembly 12 is shown to illustrate how gamma rays pass through the pinhole aperture portion 50 of the collimator assembly 12. As previously mentioned, collimator assembly 12 includes inner combined collimator 40 and outer collimator 42 with the inner combined collimator 40 including the pinhole aperture portion 50 having one or more pinhole apertures 46 therein. As illustrated by FIGS. 9 and 10, pinhole apertures 46 open in the shape of a cone from both sides of the pinhole aperture 46 to the exterior surfaces of the pinhole aperture portion 50. With this arrangement, gamma rays traveling in a direction oblique to the pinhole aperture 46 may pass through the collimator assembly 12. Accordingly, gamma rays that pass through the pinhole apertures 46 would have a cone-beam geometry, as indicated by gamma rays 30. Gamma rays not aligned with the pinhole apertures 46 would not pass through the collimator assembly 12. In the illustrated embodiment, the pinhole aperture 46 is defined by angled segments 70 of the pinhole aperture portion 50 of the inner combined collimator 40. Those of ordinary skill in the art will appreciate that varying the angle of the angle segments 70 should affect the field of view of the pinhole, the extent of potential overlap of the projected pinhole cone-beams on the detector assembly 14, the sensitivity of the pinhole, and the proportion of gamma rays that penetrate the edges of the pinhole.

Figure 11:
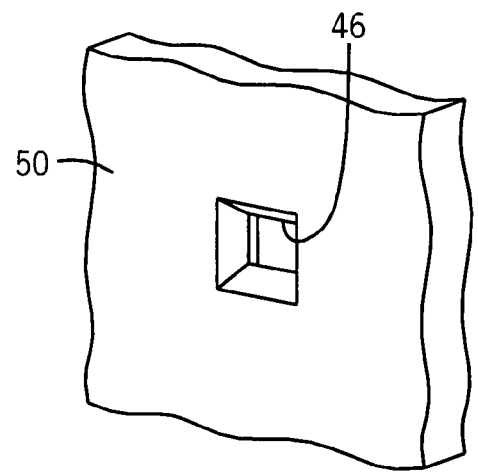
FIG. 11 is an illustration of an alternative arrangement of a pinhole aperture of an exemplary combined collimator in accordance with embodiments of the present technique.

As illustrated by FIG. 9, the pinhole aperture 46 through the pinhole aperture portion 50 may have a substantially circular configuration. Other aperture configurations, however, may also be suitable. By way of example, the pinhole aperture portion 50 of the inner combined collimator 40 may be configured as having aperture configurations that are substantially polygonal (e.g., three-sided, four-sided, five-sided, six-sided, and so forth), or substantially curved (e.g., elliptical, circular, and so forth). By way of example, FIG. 11 illustrates a perspective view of a pinhole aperture 46 through the pinhole aperture portion 50 having a substantially polygonal configuration and specifically having a substantially square configuration. Those of ordinary skill in the art will appreciate that the aperture configuration may be selected based on, inter alia, the desired resolution, sensitivity, and field of view, including consideration of the performance of the image reconstruction and processing module 18. Further, those of ordinary skill in the art will appreciate that varying the aperture configuration will generally impact the resolution, sensitivity, and field of view of the SPECT system 10. Additionally, the portion of the inner combined collimator 40 surrounding the pinhole aperture 46 may be constructed from the same or different material as that used for the photon-absorbing pinhole aperture portion 50.

Figure 12:
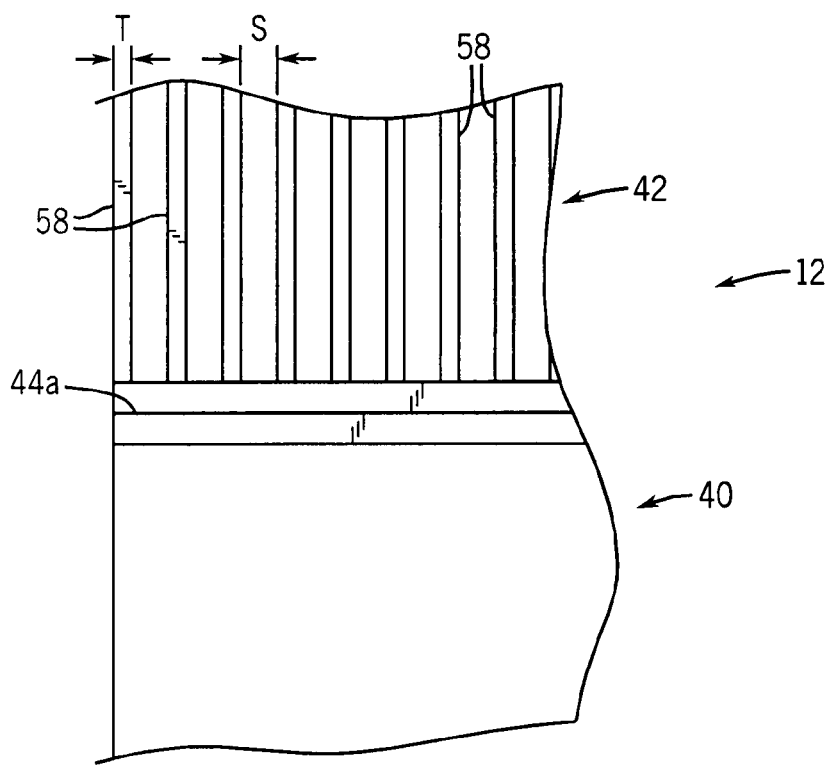
FIG. 12 is a cross-sectional view of the exemplary collimator assembly of FIG. 2 taken along line 12-12, in accordance with embodiments of the present technique.

Referring now to FIG. 12, a cross-sectional view of the collimator assembly 12 of FIG. 2 taken along line 12-12 is shown with only a portion of the septa 58 illustrated. As previously mentioned, the outer collimator 42 includes one or more septa 58 spaced on a side of the slitted portion 48 of the inner combined collimator 40 opposite from the field of view 24. The septa 58 may be made from any radiation absorbent material, such as lead or tungsten. The thickness T of the septa 58 is generally in the range of from about 0.1 mm to about 2 mm, for example. Further, the spacing S between each of the septa 58 may be in the range of from about 1 mm to about 10 mm, for example. Further, the spacing between the septa 58 may the same or different, i.e., a spacing S may separate certain septa 58, a spacing S' may separate other septa 58, and so forth. Those of ordinary skill in the art will appreciate that the number and spacing of the septa 58 must be chosen with consideration of the efficient utilization of the detector assembly 14, the desired axial resolution and sensitivity, and the performance of the image reconstruction and processing module 18.

In the illustrated embodiment, each of the septa 58 of the outer collimator 42 is arranged in parallel. Those of ordinary skill in the art will recognize that the present technique may be implemented with septa 58 having alternative configurations. By way of example, septa 58 arranged in converging or diverging configurations may also be employed. Those of ordinary skill in the art will also recognize that the parallel septa illustrated in FIG. 12 may also be slanted at an oblique angle with respect to the longitudinal axis 52, in which case the axial field of view 24 will be offset from the detector assembly 14.

Figure 13:
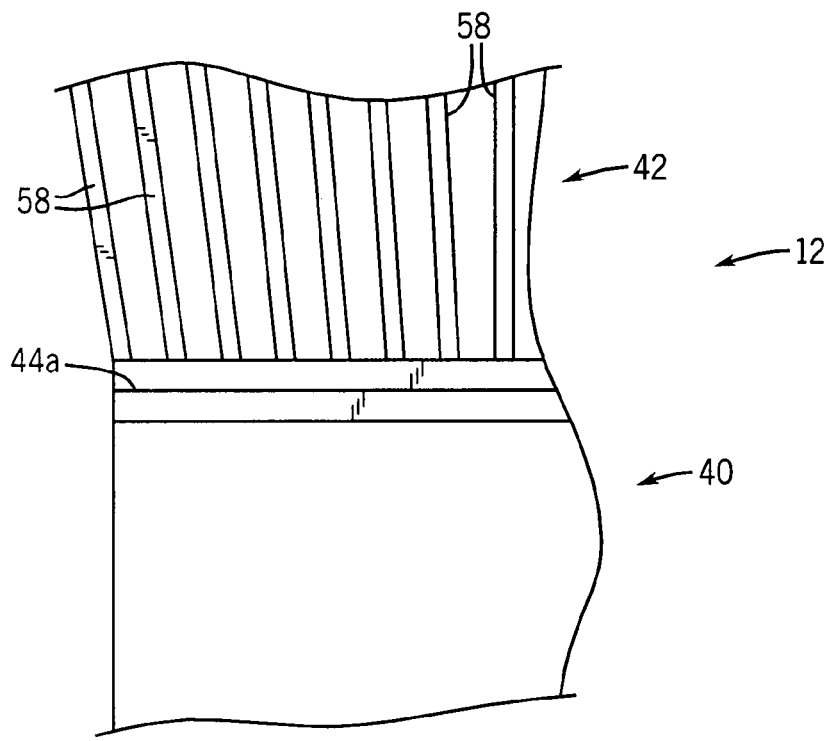
FIG. 13 is a cross-sectional view of an exemplary collimator assembly similar to that of FIG. 2 and having an alternative septa configuration, in accordance with embodiments of the present technique.

Referring now to FIG. 13, a cross-sectional view of a collimator assembly 12 is shown having an alternative septa arrangement in accordance with an exemplary embodiment of the present technique. As illustrated, the collimator assembly 12 contains an outer collimator 42 having septa 58 arranged in a diverging configuration. In the illustrated embodiment, the septa 58 are arranged to extend from the inner combined collimator 40 so as to diverge. As will be appreciated by those of ordinary skill in the art, with the septa 58 arranged in a diverging configuration, the axial length of the field of view 24 will be less than axial length of the detector assembly 14.

Figure 14:
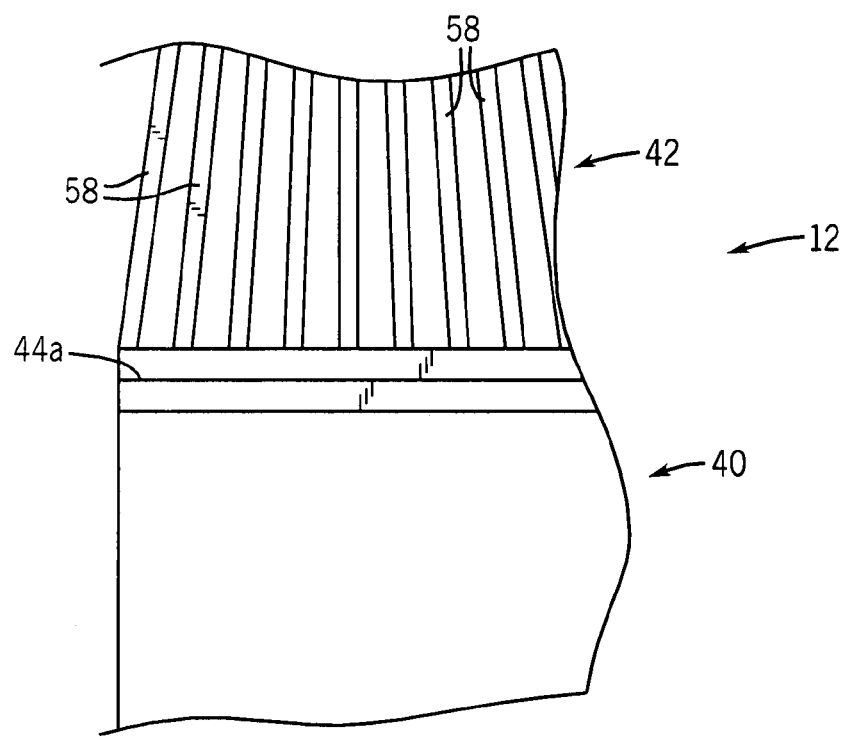
FIG. 14 is a cross-sectional view of an exemplary collimator assembly similar to that of FIG. 2 having another alternative septa configuration, in accordance with embodiments of the present technique.

Referring now to FIG. 14, a cross-sectional view of a collimator assembly 12 is shown having another alternative blade arrangement in accordance with an exemplary embodiment of the present technique. As illustrated, the collimator assembly 12 contains an outer collimator 42 having septa 58 arranged in a converging configuration. In the illustrated embodiment, the septa 58 are arranged to extend from the inner combined collimator 40 so as to converge. As will be appreciated by those of ordinary skill in the art, with the septa 58 arranged in a converging configuration, the axial length of the field of view 24 will be greater than axial length of the detector assembly 14.

Moreover, those of ordinary skill in the art will recognize that the SPECT system 10 may require calibration. Calibration of the SPECT system 10 may require, for example, use of a radioactive source without the subject 28 present in the field of view 24. In general, slit collimators typically require line sources while pinhole collimators require point sources. As such, the SPECT system 10 comprising the inner combined collimator 40 may require calibration with both a line source and point source. A line source may be effectively simulated by attaching a point source to the subject support 26 and moving the support and point source to multiple positions either continuously or in a step and shoot manner during the calibration.

Figure 15:
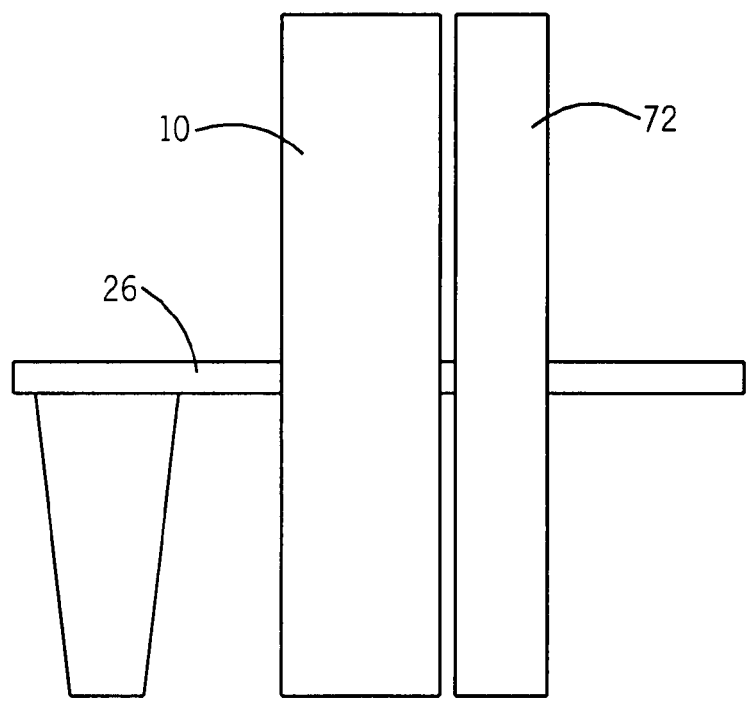
FIG. 15 is an illustration of an exemplary combined SPECT and computed tomography (CT) system in accordance with embodiments of the present technique.
Figure 16:
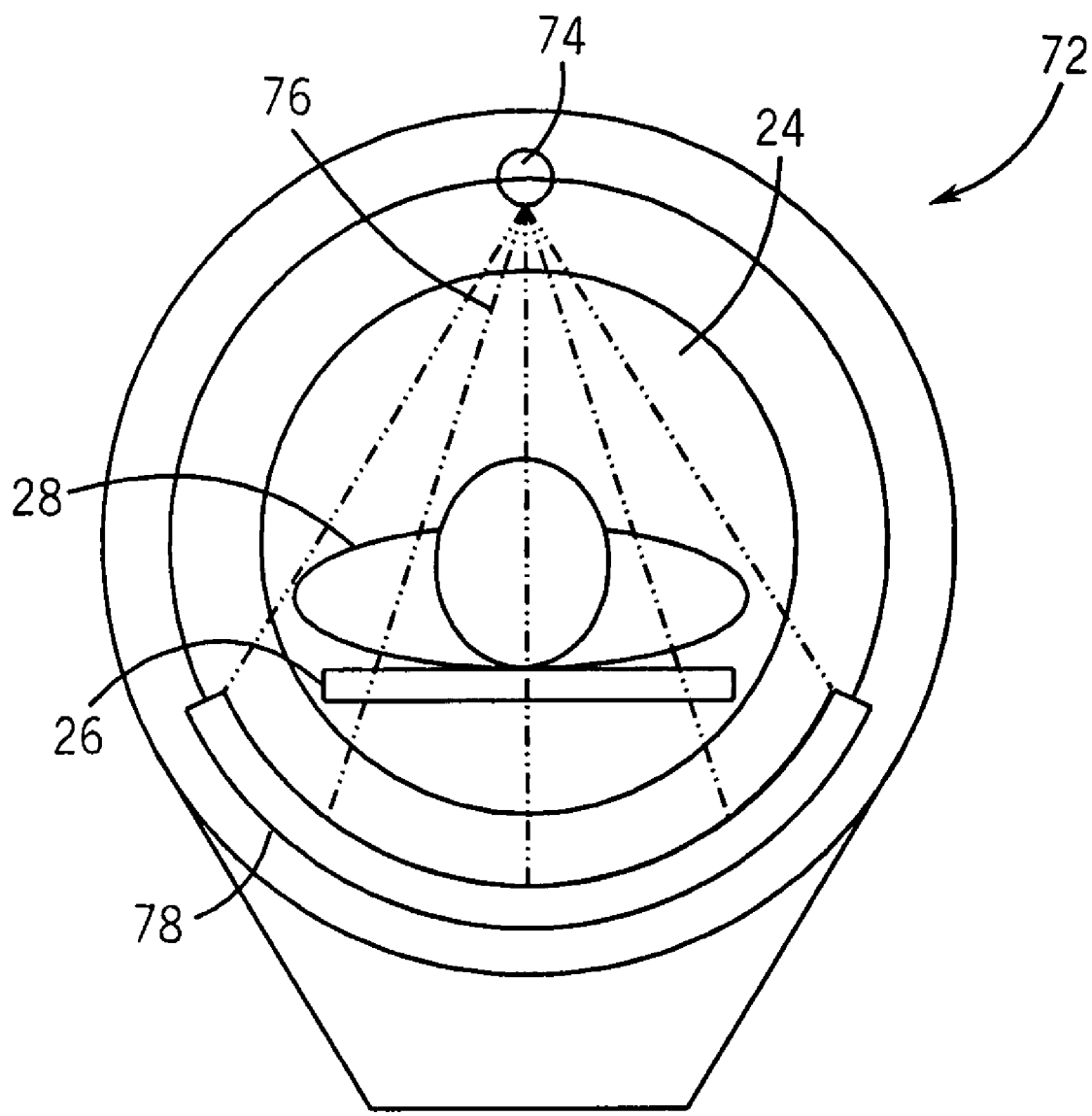
FIG. 16 is an illustration of an exemplary CT system that can be combined with a SPECT system, in accordance with embodiments of the present technique.

While specific reference in the present discussion is made to a SPECT system, it should be appreciated that the present technique is not intended to be limited to this or any other specific type of imaging system or modality. Rather, exemplary embodiments of the present technique may be used in conjunction with other imaging modalities, e.g., coded-aperture astronomy. In addition, SPECT system 10 may be combined with a second imaging system, such as a CT system or a magnetic resonance imaging (MRI) system. By way of example, the SPECT system 10 may be combined in the same gantry with a CT system. As illustrated in FIG. 15, a SPECT/CT imaging system includes SPECT system 10 and CT system 72. By way of example, the SPECT system 10 and the CT system 72 are shown as separate modules, aligned along a common longitudinal axis, and sharing a single subject support 26. As illustrated by FIG. 16, CT system 72 includes a source 74 of X-ray radiation configured to emit a stream of radiation 76 in the direction of the field of view 24 and an X-ray detector assembly 78 configured to generate one or more signals in response to the stream of radiation. Those of ordinary skill in the art will appreciate that in the third-generation CT configuration illustrated in FIG. 16, the source 74 and the X-ray detector assembly 78 generally rotate in synchrony around the field of view while acquiring a plurality of lines of response passing through the subject, so that an X-ray tomographic attenuation image may be reconstructed. Other CT configurations may be employed, including the shared use of at least a portion of the SPECT detector assembly 14 as the X-ray detector assembly 78. Further, the SPECT and CT images may be acquired sequentially, in any order, by repositioning the subject, or concurrently by sharing the detector array. The images generated with the CT system 72 may then be used to generate gamma ray attenuation maps, for example, to calculate attenuation and/or scatter correction during the SPECT image reconstruction. In addition, the CT anatomical images may be combined with the SPECT functional images.

While only certain features of the invention have been illustrated and described herein, many modifications and changes will occur to those skilled in the art. It is, therefore, to be understood that the appended claims are intended to cover all such modifications and changes as fall within the true spirit of the invention.

The invention claimed is:

1. A collimator assembly comprising:
   an inner combined collimator comprising a first portion having one or more slit apertures therein, and a second portion having one or more pinhole apertures therein; and
   an outer collimator comprising one or more septa spaced on a side of the first portion of the inner combined collimator, wherein the slit apertures of the inner combined collimator and the septa of the outer collimator are arranged to define a plurality of apertures for gamma rays emanating from a field of view.

2. The collimator assembly of claim 1, wherein the slit apertures are generally orthogonal to the septa of the outer collimator.

3. The collimator assembly of claim 1, wherein the slit apertures are generally oblique to the septa of the outer collimator.

4. The collimator assembly of claim 1, wherein the collimator assembly comprises a longitudinal axis, wherein the slit apertures extend in a direction generally parallel to the longitudinal axis of the collimator assembly.

5. The collimator assembly of claim 1, wherein the collimator assembly comprises a longitudinal axis, wherein the slit apertures extend in a direction generally orthogonal to the longitudinal axis of the collimator assembly.

6. The collimator assembly of claim 1, wherein the collimator assembly comprises a longitudinal axis, wherein the slit apertures extend in a direction generally diagonal to the longitudinal axis of the collimator assembly.

7. The collimator assembly of claim 1, wherein each of the slit apertures has a width in the range of from about 0.1 mm to about 10 mm, each of the pinhole apertures have a width in the range of from about 0.1 mm to about 10 mm, and/or the septa are spaced at a width in the range of from about 0.1 mm to about 10 mm.

8. The collimator assembly of claim 1, wherein the plurality of septa are arranged in parallel with respect to one another, wherein the plurality of septa are arranged to extend from the inner combined collimator so as to converge, or wherein the plurality of septa are arranged to extend from the inner combined collimator so as to diverge.

9. The collimator assembly of claim 1, wherein the inner combined collimator is generally cylindrically shaped.

10. The collimator assembly of claim 1, wherein the slit aperture edges and the pinhole aperture edges are sharp or blunted.

11. The collimator assembly of claim 1, wherein the slit apertures include slits apertures with two or more different widths, the pinhole apertures include pinhole apertures with two or more different widths, and/or the one or more septa include a plurality of septa spaced at two or more different widths on the first side of the inner combined collimator.

12. The collimator assembly of claim 1, wherein the inner combined collimator comprises a radiation absorbent material.

13. An imaging system, comprising:
   a collimator assembly comprising an inner combined collimator and an outer collimator, the inner combined collimator comprising a first portion having one or more slit apertures therein and a second portion having one or more pinhole apertures therein, the outer collimator comprising one or more septa spaced on a side of the first portion of the inner combined collimator opposite from a field of view, wherein the slit apertures of the inner combined collimator and the septa of the outer collimator are arranged to define a plurality of apertures for gamma rays emanating from a field of view; and
   a detector assembly configured to detect gamma rays emanating from the field of view that pass through one or more apertures defined by the collimator assembly and to generate one or more signals in response to the detected gamma rays.

14. The imaging system of claim 13, wherein the slit apertures are generally orthogonal to the septa of the outer collimator.

15. The imaging system of claim 13, wherein the slit apertures are generally oblique to the septa of the outer collimator.

16. The imaging system of claim 13, wherein the collimator assembly comprises a longitudinal axis, wherein the slit apertures extend in a direction generally parallel to the longitudinal axis of the collimator assembly.

17. The imaging system of claim 13, wherein the collimator assembly comprises a longitudinal axis, wherein the slit apertures extend in a direction generally orthogonal to the longitudinal axis of the collimator assembly.

18. The imaging system of claim 13, wherein the collimator assembly comprises a longitudinal axis, wherein the slit apertures extend in a direction generally diagonal to the longitudinal axis of the collimator assembly.

19. The imaging system of claim 13, wherein the inner combined collimator extends from 180° to 360° around the field of view.

20. The imaging system of claim 13, wherein the detector assembly comprises at least one of an array of solid-state detector elements or a scintillator assembly coupled to light sensors.

21. The imaging system of claim 13, wherein one or both of the collimator assembly and the detector assembly are configured to rotate.

22. The imaging system of claim 13, comprising a support for supporting a subject in the field of view.

23. The imaging system of claim 13, comprising:
   a module configured to receive the one or more signals and to process the one or more signals to generate one or more images; and
   an image display workstation configured to display the one or more images.

24. The system of claim 13, comprising a source of X-ray radiation configured to emit a stream of radiation in the direction of the field of view.

25. A method of imaging a volume, comprising:
   positioning at least a portion of a subject in a field of view of a single photon emission computed tomography system;

collimating gamma rays emitted from the portion of the patient using a collimator assembly, the collimator assembly comprising an inner combined collimator and an outer collimator, the inner combined collimator comprising a first portion having one or more slit apertures therein, and a second portion having one or more pinhole apertures therein, the outer collimator comprising one or more septa spaced on a side of the first portion of the inner combined collimator opposite from the field of view such that the slit apertures and the septa define one or more pathways through the collimator assembly;

wherein gamma rays aligned with one of the pinhole apertures, and gamma rays aligned with the one of the pathways defined by the slit apertures and the spaced septa of the outer collimator pass through the collimator assembly, and wherein gamma rays not aligned with one of the pinhole apertures or one of the pathways are absorbed by the collimator assembly;

detecting the gamma rays that pass through the collimator assembly; and generating one or more signals in response to the detected gamma rays.

26. The method of claim 25, comprising:

processing the one or more signals to generate one or more images; and displaying the one or more images on an operator workstation.

27. The method of claim 25, comprising rotating one or both of the collimator assembly and the detector array.

28. The method of claim 25, comprising acquiring anatomical images and single photon emission computed tomography images.

\* \* \* \* \*